United States Patent
Ruimi

(10) Patent No.: US 6,324,246 B1
(45) Date of Patent: Nov. 27, 2001

(54) HELICAL SCANNER WITH VARIABLY ORIENTED SCAN AXIS

(75) Inventor: David Ruimi, Netanya (IL)

(73) Assignee: Marconi Medical Systems Israel Ltd., Haifa (IL)

( * ) Notice: Subject to any disclaimer, the term of this patent is extended or adjusted under 35 U.S.C. 154(b) by 0 days.

(21) Appl. No.: 09/367,771
(22) PCT Filed: Feb. 20, 1997
(86) PCT No.: PCT/IL97/00069
§ 371 Date: Nov. 22, 1999
§ 102(e) Date: Nov. 22, 1999
(87) PCT Pub. No.: WO98/36689
PCT Pub. Date: Aug. 27, 1998

(51) Int. Cl.[7] ................................. A61B 6/03
(52) U.S. Cl. ....................... 378/15; 378/17; 378/901
(58) Field of Search ..................... 378/4, 8, 15, 17, 378/94

(56) References Cited

U.S. PATENT DOCUMENTS

| 5,291,402 | 3/1994 | Pfoh | 378/13 |
| 5,485,493 | 1/1996 | Heuscher | 378/15 |
| 5,513,236 | 4/1996 | Hui | 378/15 |
| 5,515,409 | 5/1996 | Hsieh | 378/15 |
| 6,118,841 | * 9/2000 | Lai | 378/19 |

OTHER PUBLICATIONS

Ogawa et al.: "Improvement of Image Quality by Tilted Fan Beam Acquisition in a Helical Scan X–ray CT" 1996 IEEE Nuclear Science Symposium Conference Record, vol. 2, Nov. 2–9, 1996; New York, US, pp. 1448–1452, XP002047533.

* cited by examiner

Primary Examiner—David V. Bruce
(74) Attorney, Agent, or Firm—Fenster & Company Patent Attorneys, Ltd.

(57) ABSTRACT

A method for reconstructing images of a subject in a variable-angle helical-scan CT scanner including an X-ray tube, a detector array, and a bed, the method comprising: angling the translation axis and the rotation axis at an acute angle relative to one another; rotating the X-ray tube about the rotation axis while translating the bed along the translation axis through a plane of rotation of the tube, whereby the X-ray tube describes a helical path relative to the subject; acquiring first and second views of the subject at the same effective rotational angle about the axis of rotation, said views comprising X-ray attenuation data received from elements of the array; producing a planar corrected image slice by interpolation of the data in different views, wherein the data is generated by non-corresponding elements in the different views; and repeating the above steps at respective positions at a plurality of rotational angles of the X-ray tube.

23 Claims, 4 Drawing Sheets

HELICAL SCANNER WITH VARIABLY ORIENTED SCAN AXIS

RELATED APPLICATION

This application is a U.S. National filing PCT Application PCT/IL97/00069, filed Feb. 20, 1997.

FIELD OF THE INVENTION

The present invention relates generally to computerized tomographic (CT) imaging, and specifically to multi-slice CT scanners having helical scan paths.

BACKGROUND OF THE INVENTION

Helical-path CT scanners are well known in the art. Generally, such scanners comprise an X-ray tube, mounted on an annular gantry, so as to rotate continuously about a subject being imaged. The subject lies on a table, which is translated continuously through the gantry simultaneously with the gantry's rotation, while X-ray detectors on the opposite side of the subject from the X-ray tube receive radiation transmitted through the subject. The axis of translation of the bed is generally parallel to the long axis of the subject's body, which is typically perpendicular to the plane of rotation of the gantry. Thus, the path of the X-ray tube relative to the subject generally describes a helix about this axis, and X-ray attenuation data received from the X-ray detectors similarly correspond to a series of helically-disposed "views" through the subject. In order to reconstruct planar cross-sectional image slices of the subject, attenuation data for each point in such a planar slice are derived by interpolation between data points in the original helical-path views.

Multi-slice helical-path scanners are similarly known in the art. For example, U.S. Pat. No. 5,485,493, which is incorporated herein by reference, describes a multiple detector ring spiral scanner with relatively adjustable helical paths, in which two or more adjacent, parallel slices are acquired along two or more parallel paths simultaneously or sequentially. Data corresponding to planar slices are derived by interpolating between data acquired along the two helical paths. Helical-path scanners in which more than two slices are acquired are also known in the art.

In some scanners, the long axis of the subject's body, along which direction the bed is translated, may be angled relative to the plane of rotation of the gantry, rather than being perpendicular to the axis, as in conventional scanners. This angling typically includes swiveling the bed about a vertical axis, tilting the gantry about a horizontal axis, or a combination of swiveling and tilting. Since the image views are similarly angled relative to the body axis, this angling function is frequently useful in resolving image features that may be difficult to observe in conventional, non-angled scanning. For example, bed swivel may be used in generating longitudinal image slices through the pancreas, and variable gantry tilt may be used to generate images of angled, sectional cuts through the disc spaces of the spine.

When the body axis is tilted, the scanning path of the X-ray tube relative to the axis no longer describes a simple, constant-pitch helix, but rather a more complex spiral figure. In this case, accurate interpolation between different points acquired along a helical path, for the purpose of reconstructing corrected planar image slices, becomes considerably more complicated. Improper selection of the points for interpolation can produce artifacts in the reconstructed image.

SUMMARY OF THE INVENTION

It is an object of the present invention to provide a method for accurate image reconstruction based on angled helical-scan CT data.

In one aspect of the present invention, angled helical scan data generated during different positions of the gantry (i.e., at different helical positions of the gantry) are combined to form a data set of a view for reconstruction of the image. Due to the geometry of the system this requires that data from non-corresponding elements be combined, where corresponding elements are defined as:

for 360 degree reconstruction, as elements having the same circumferential position; and for 180 degree reconstruction, as elements having the same circumferential distance from an element corresponding to the center of rotation of the gantry, on opposite sides of that element.

In one aspect of the present invention, the helical-scan data are used to reconstruct planar corrected image slices.

In another aspect of the present invention, the CT data comprise multiple-slice CT data, acquired using a multi-row detector array.

In preferred embodiments of the present invention, a variable-angle multi-slice helical-scan CT scanner comprises an X-ray tube, mounted on an annular gantry, which rotates about a bed on which a subject lies, and a detector array. The X-ray tube irradiates the subject from multiple points along its helical trajectory. The detector array comprises one or more parallel rows of X-ray detector elements, each row having a long axis disposed in a generally circumferential direction with respect to the long axis of the subject's body. The detector elements receive radiation that has passed through the subject's body and generate signals responsive to attenuation of the X-rays. The bed is advanced through the gantry along a translation axis that is generally parallel to the long axis of the subject's body. The gantry tilts about a horizontal axis, and the bed swivels, relative to the gantry, about a vertical axis, so that the translation axis of the bed describes an acute angle relative to the axis of rotation of the gantry. The scanner thus performs an angled helical scan over at least a portion of the body.

For each view, i.e., each position of the X-ray tube relative to the body at which X-ray attenuation signals are received from the detector array, the detector array generates a matrix of attenuation signals. Each row in the signal matrix corresponds to a row of elements in the detector array. These signals are normalized and undergo a log operation, as is known in the art. Preferably, the resultant data are then interpolated to generate geometrically-corrected CT data, which are associated with planar slices through the body. These slices are generally perpendicular to the gantry rotation axis, and are therefore swiveled and/or tilted with respect to the long axis of the body. The corrected data in these planar slices are filtered and back-projected to reconstruct a three-dimensional CT image of the subject's body, using methods known in the art.

Alternatively, instead of interpolating the normalized, log data, the "raw" signals may first be interpolated before undergoing the log operations. Further alternatively, the data may be interpolated after the filtering or after the back-projection operation. It will be appreciated that the principles of the present invention may be applied in these cases, as well.

In preferred embodiments of the present invention, the geometrically-corrected CT data comprise effective attenuation values with respect to each of the planar slices. For each slice, these values are calculated for a plurality of effective detection points, geometrically fixed along a periphery of the slice. Each of the effective attenuation values corresponds to the approximate attenuation that would have been measured along a ray in the planar slice from the X-ray tube to the location of the effective detection point, at a given rotation angle of the tube about the gantry's axis of rotation The effective attenuation values for each planar slice are calculated for a plurality of rotation angles, preferably covering 360° of rotation about the axis (or more, depending on the helix angle). These values are filtered and back-projected using 360° CT image reconstruction, as is known in the art. Reconstruction using single slices requires at least two rotations and generally more, depending on the helix angle.

Alternatively, 180° reconstruction may be used, as described in an Israel Application filed on even date with the present application, entitled "On-Line Image Reconstruction in Helical CT Scanners" by Elscint Ltd., assignee of the present application, and incorporated herein by reference. In this case, the effective attenuation values for each planar slice are calculated for a plurality covering only about 180° of rotation.

Although the effective detection points are fixed in the plane of the slice, the actual elements of the detector array are generally not in this plane. The positions of the actual elements relative to the effective detection points vary from one tube rotation angle to another, due to the helical shape of the scan path. Therefore, for each of the effective detection points at each rotation angle, two or more detector elements are selected. The elements selected are those whose positions are geometrically closest to the position of the effective detection point at that rotation angle. The actual, measured attenuation data at the element positions are interpolated to calculate the corresponding effective attenuation value at the effective detection point.

In preferred embodiments of the present invention in which a multi-row detector array is used, the actual elements selected for some rotation angles will be mutually-adjacent elements in adjoining, parallel rows of the array. In this case, the effective attenuation values are interpolated from measured attenuation data from adjacent rows of the signal matrix at a single view, i.e., signals that are acquired while the X-ray tube is at one, given position along the helical scan path.

For other rotation angles, however, and for every rotation angle in preferred embodiments of the present invention in which a single-row detector array is used, the effective attenuation values are interpolated from two or more different signal matrix rows, acquired at different views of the X-ray tube along the helical scan path. In preferred embodiments using 360° reconstruction, the different views are separated by a 360° rotation of the gantry, which is accompanied by translational motion of the bed through the gantry. Additional data may be acquired during further rotations. Alternatively, in 180° reconstruction systems, the different views are separated by 180° of rotation of the gantry. Data can also be acquired from subsequent 180 degree rotations.

In such cases, in which signals from different views are combined, the actual detector elements whose positions are closest to any one of the effective detection points are typically not mutually adjacent elements of the array. The tilt and/or swivel of the scanner introduces an offset, dependent on the rotation angle, between the positions of the elements. In accordance with preferred embodiments of the present invention, the actual detector elements corresponding to each effective detection point are selected based on the tilt and/or swivel angles, the rotation angle, the pitch of the helical path, and other geometrical considerations. Failure to take any of these aspects into account will typically result in artifacts appearing in the CT image.

In some preferred embodiments of the present invention, each effective attenuation value, for each effective detection point, is calculated by weighted interpolation between actual attenuation values derived from two different signal matrix rows. Weighting factors for the interpolation at each point are preferably determined based on the respective distances between the point and the positions of the corresponding actual detector elements. Most preferably, the element closest to the point has the largest weighting factor.

In other preferred embodiments of the present invention, the effective attenuation values are calculated by weighted interpolation between elements in three or more different signal matrix rows. The wider range of interpolation is useful in reducing noise and artifacts in the resultant image. Here, too, the weighting factors are preferably dependent on the distances between each of the effective detection points and the corresponding actual detector elements, as described above.

It will be appreciated that while the preferred embodiments described herein make reference to certain types of medical CT imaging systems, which form an image of the body of a human subject the principles of the present invention may similarly be applied to other types of CT imaging systems for medical and non-medical purposes.

There is thus provided, in accordance with a preferred embodiment of the invention, a method for reconstructing images of a subject in a variable-angle helical-scan CT scanner, said scanner including an X-ray tube mounted for rotation about a rotation axis, a detector array having one or more rows of detector elements that generate signals responsive to X-rays incident thereon, and a bed, translatable along a translation axis, on which bed the subject is placed, said method comprising:

angling the translation axis and the rotation axis at an acute angle relative to one another;

rotating the X-ray tube about the rotation axis while translating the bed along the translation axis through a plane of rotation of the tube, whereby the X-ray tube describes a helical path relative to the subject;

acquiring first and second views of the subject at the same effective rotational angle about the axis of rotation, said views comprising X-ray attenuation data received from elements of the array;

producing a planar corrected image slice by interpolation of the data in different views, wherein the data is generated by non-corresponding elements in the different views; and repeating the above steps at respective positions at a plurality of rotational angles of the X-ray tube.

Preferably, producing the planar corrected image slice comprises:

finding a first row of detector elements in one of the first and second views having a longitudinal axis that is closest to a plane of the image slice;

finding a second row of detector elements in one of the first and second views having a longitudinal axis that is next closest to the plane after the first row;

determining a first attenuation value from the first row of elements and a second attenuation value from the second row of elements; and calculating an effective attenuation value by weighted interpolation of the first and second attenuation values.

In a preferred embodiment of the invention, finding first and second rows of detector elements comprises finding two adjoining rows of the detector array in one of the first and second views.

Preferably, finding first and second rows of detector elements comprises finding a first row in the first view and a second row in the second view, and wherein determining first and second attenuation values comprises determining an offset between the first and second rows. In a preferred embodiment of the invention, determining the offset between the first and second rows comprises determining an offset dependent on the rotational angle of the X-ray tube. Preferably, determining the offset between the first and second rows comprises determining an offset dependent on the acute angle between the translation axis and the rotation axis.

In a preferred embodiment of the invention determining the first attenuation value comprises computing a weighted sum of attenuation data received from two or more detector elements in the first row. Preferably, determining the second attenuation value comprises computing a weighted sum of attenuation data received from two or more detector elements in the second row.

In a preferred embodiment of the invention, calculating the effective attenuation value by weighted interpolation comprises determining weighting factors dependent on the rotational angle of the X-ray tube. Alternatively or additionally calculating the effective attenuation value by weighted interpolation preferably comprises determining weighting factors dependent on the acute angle between the translation axis and the rotation axis.

In a preferred embodiment of the invention determining the first attenuation value at a point in the view comprises finding the two elements in the first row whose centroids are closest to the point and calculating an effective row element attenuation value based on signals received from the two elements. Alternatively or determining the second attenuation value at a point in the view preferably comprises finding the two elements in the second row whose centroids are closest to the point and calculating an effective row element attenuation value based on signals received from the two elements.

In a preferred embodiment of the invention the method includes finding one or more additional rows of detector elements, parallel to the first and second rows, and determining one or more additional attenuation values from the additional rows, wherein calculating an effective attenuation value in the planar slice comprises calculating the effective attenuation value by weighted interpolation of the additional values with the first and second attenuation values.

In a preferred embodiment of the invention the method comprises acquiring one or more additional views at the same effective rotational angle as the first and second views, wherein producing the planar corrected image slice by interpolation of the data in the views comprises combining the one or more additional views with the first and second views by weighted interpolation of the data.

In a preferred embodiment of the invention, the detector array has one row of elements. In an alternative preferred embodiment of the invention, the detector array has more than one row of elements.

There is further provided, in accordance with a preferred embodiment of the invention, a method for reconstructing images of a subject in a variable-angle helical-scan CT scanner, said scanner including an X-ray tube mounted for rotation about a rotation axis, a detector array having one or more rows of detector elements that generate signals responsive to X-rays incident thereon, and a bed, translatable along a translation axis, on which bed the subject is placed, the method comprising:

angling the translation axis and the rotation axis at an acute angle relative to one another;

rotating the X-ray tube about the rotation axis while translating the bed along the translation axis through a plane of rotation of the tube, whereby the X-ray tube describes a helical path relative to the subject;

acquiring first and second views of the subject at first and second positions along the helical path of the X-ray tube, both positions being at the same effective rotational angle about the axis of rotation, said views comprising X-ray attenuation data received from elements of the array;

producing a planar corrected image slice by interpolation of the data in different views; and repeating the above steps at respective positions at a plurality of rotational angles of the X-ray tube, wherein determining a value for interpolation at a point in the view comprises finding the two elements in a row whose centroids are closest to the point and calculating an effective row element attenuation value based on signals received from the two elements.

In a preferred embodiments of the above described invention acquiring said first and second views comprises acquiring said first and second views at first and second positions along the helical path of the X-ray tube.

The present invention will be more fully understood from the following detailed description of the preferred embodiments thereof, taken together with the drawings in which:

DETAILED DESCRIPTION OF PREFERRED EMBODIMENTS

Figure 1:
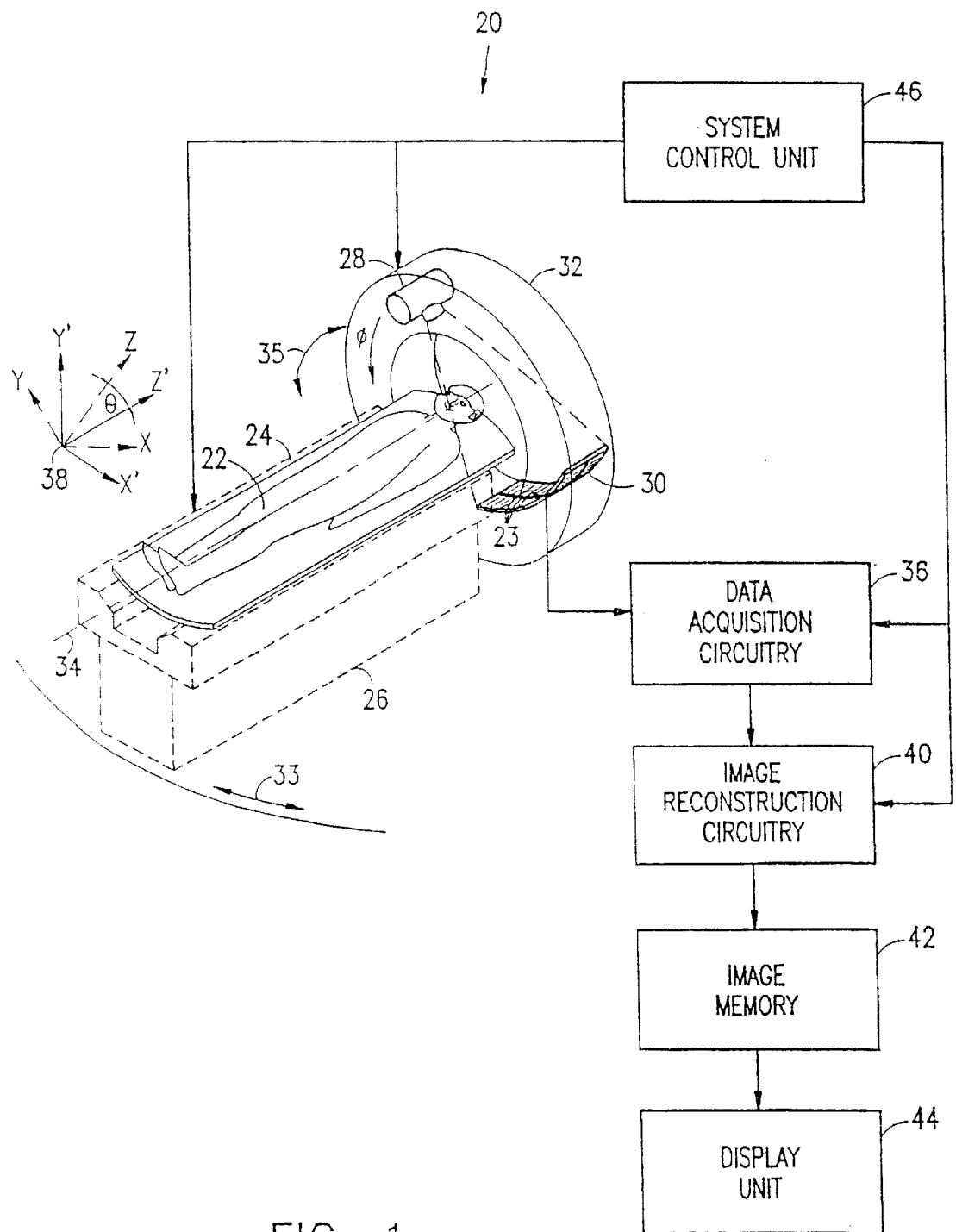
FIG. 1 is a schematic illustration of a variable-angle, multi-slice helical-scan CT scanner, operative in accordance with a preferred embodiment of the present invention.

Reference is now made to FIG. 1, which shows a CT scanner 20, operative in accordance with a preferred embodiment of the present invention. Scanner 20 comprises a bed 24, supported by a base 26, on which bed a subject 22 lies while his body is being imaged by the scanner. Scanner 20 further comprises an X-ray tube 28, which irradiates subject 22, and a detector array 30, which receives X-rays from tube 28 and generates signals responsive to the attenuation of the X-rays in passing through the subject's body. Preferably, array 30 comprises multiple, parallel rows of X-ray detector elements 23. Tube 28 and array 30 are mounted on an annular gantry 32, so as to rotate about subject 22. Simultaneously, bed 24 is advanced through gantry 32 along axis 34, which is generally parallel to the long axis of the subject's body.

Scanner 20 as pictured in FIG. 1 is of a type known in the art as a third-generation CT-scanner, characterized in that both tube 28 and detector array 30 rotate about subject 22. It will be appreciated, however, that the principles of the present invention and the methods of image reconstruction to be described below are equally applicable to other types of CT scanners, for example, fourth-generation CT scanners, which include annular detector arrays that are generally rotationally stationary, while the X-ray tube rotates about the subject.

Scanner 20 may be configured so that axis 34 is substantially perpendicular to the plane of rotation of gantry 32. Additionally, axis 34 may preferably be angled relative to the gantry plane, for example, by swiveling bed 24 horizontally, in a direction indicated by arrow 33, and/or by tilting gantry 32 about a generally horizontal tilt axis in a direction indicated by arrow 35. Preferably, the tilt and swivel angles are controlled by a system control unit 46, which also regulates the rotation of the gantry and the advance of the bed.

For clarity in the following discussion, we identify two sets of Cartesian coordinate axes 38 in FIG. 1: rotating, gantry-fixed axes X, Y, Z, indicated by dashed arrows, and bed-fixed axes X', Y', Z', indicated by solid arrows. The Z-axis is substantially the axis of rotation of gantry 32 and is fixed in space. The Y-axis points from the center of rotation of the gantry to tube 28 and rotates therewith, and the X-axis is, therefore, generally parallel to the long axis of array 30. The Z'-axis is parallel to bed axis 34. Axis Y' points vertically upward, parallel to the swivel axis (if any) of bed 24, and axis X' is thus generally horizontal. Axis Z' is angled relative to axis Z by a two-dimensional angle $\theta$, which takes into account both the tilt of gantry 32 and the swivel of bed 24. The angle of rotation of the gantry $\phi$ is taken to be zero when tube 28 is at its uppermost rotational position.

As tube 28 rotates and bed 24 advances, the tube describes a generally spiral path around axis 34. Preferably, bed 24 moves with substantially constant velocity, so that the spiral path has a constant pitch. At each "view," i.e., at each of a plurality of selected locations of tube 28 along this path, data acquisition circuitry 36 acquires a matrix of attenuation signals. The elements of this matrix are signals received from each detector element 23 of array 30 responsive to X-ray attenuation along a ray from tube 28 to the detector element. Each such matrix may comprise a plurality of rows, wherein each such row corresponds to signals received at one of the plurality of views from one of the multiple rows of array 30.

For each view, data acquisition circuitry 36 performs signal normalization and logarithm operations, as are known in the art, to derive an X-ray attenuation value corresponding to each of elements 23. Image reconstruction circuitry 40 receives these values and performs interpolation and other data processing operations, as will be described below, to convert the views acquired during the helical scan into corrected, planar image slices at desired positions along the Z-axis. These planar image slices may then be used to reconstruct three-dimensional or other CT images of the body of subject 22, using methods known in the art. Preferably, these images are stored in image memory 42, displayed by display unit 44, and may be otherwise printed and/or processed as is known in the art. The data and/or images may also be stored for later reconstruction and or display.

Figure 2A:
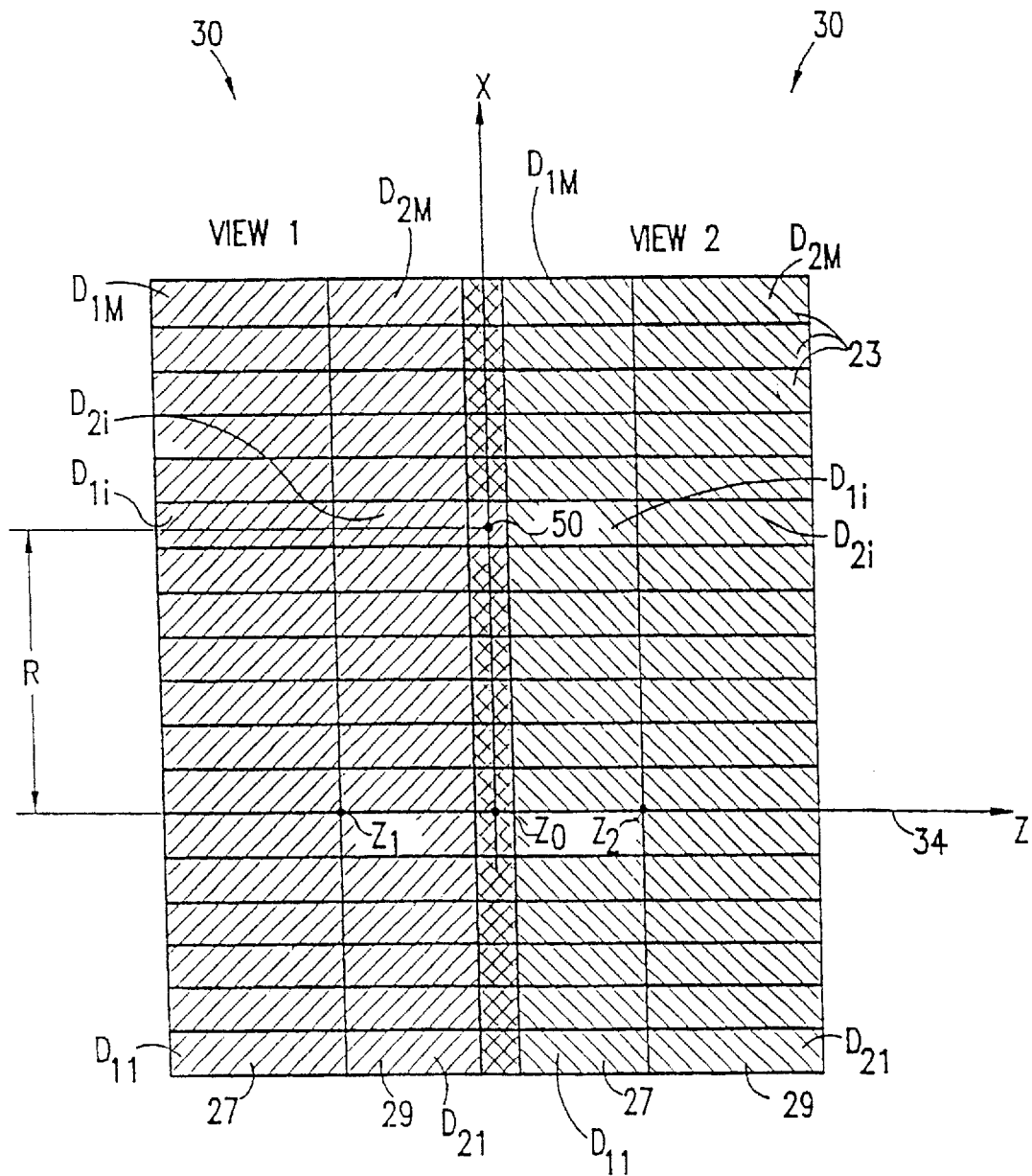
FIG. 2A is a schematic representation of detector elements in an array over two successive 360 degree rotations, incorporated in the CT scanner of FIG. 1, at a first rotation angle of the scanner (at zero or 180 degrees), illustrating geometrical principles applied in a preferred embodiment of the present invention.

FIG. 2A schematically represents the positions and detection areas of detector elements 23 in array 30 in two views, labeled "VIEW 1" and "VIEW 2." The two views are acquired at the same effective rotational angle of gantry 32, i.e., at rotation angles $\phi=0°$ and $\phi=360°$, respectively. (The same results apply for $\phi=180°$ and $\phi=540°$. In the description that follows and in the claims, two views will be said to be acquired at the same effective rotational angle when they are acquired at gantry positions separated by an integer number of full, 360° rotations, for the case of 360° reconstruction, or by an integer number of half, 180° rotations, for 180° reconstruction.

For simplicity of explanation, array 30 is shown as having only two parallel rows 27 and 29 of detectors 23, each row comprising M detector elements 23, labeled $D_{11} \ldots D_{1M}$ and $D_{21} \ldots D_{2M}$ respectively. Gantry 32 is assumed to be tilted by angle $\theta$ relative to bed 24, while the swivel angle of bed 24 is substantially zero. It will be understood, however, that the principles of the method to be described below are equally applicable to multi-slice arrays having greater or lesser numbers of rows, and to configurations of scanner 20 in which bed 24 has a non-zero swivel angle. Similarly, the method applies generally for any rotational angle $\theta$ of tube 28, as will be shown below.

In an exemplary embodiment of the invention, to acquire a matrix of attenuation signals for the first of the two views, VIEW 1, the bed 24 is advanced through gantry 32 so that array 30 is centered at a position marked $Z_1$ in the figure. As the bed continues to advance in the positive Z'-direction, gantry 32 makes a complete, 360° revolution about the bed. The gantry returns to the rotational position that it held in VIEW 1 when the array is centered at position $Z_2$, where the signal matrix for VIEW 2 is acquired. Because VIEW 1 and VIEW 2 are acquired at the same effective rotational angle $\phi=0$, and zero swivel angle, the positions of rows 27 and 29 in the two views, as shown in FIG. 2A, are mutually substantially aligned.

A planar image slice is to be reconstructed in a plane parallel to the rotation plane of gantry 32, at the position marked $Z_0$. In the situation illustrated by FIG. 2A, there is no view acquired that includes a row 27 or 29 centered at $Z_0$. A corrected slice at this position is reconstructed by choosing and interpolating between a plurality of effective detection points around a periphery of the corrected slice, at a radial distance from the Z-axis that is generally equal to the distance of the detection points in rows 27 and 29 of array 30 from the Z axis. An effective attenuation value is determined at each of the points by interpolating between the X-ray attenuation data received from two or more elements 23 in different rows 27 and 29 and/or in different views, VIEW 1 and VIEW 2. The effective attenuation at each of the plurality of points corresponds, in close approximation, to the attenuation that would be measured along a line in the X-Y plane from X-ray tube 28 to the point.

For example, to determine an effective attenuation value at a point 50, which is located on the periphery of the slice at $Z_0$, at a displacement R along the X axis as shown, a weighted sum is taken of data input from element $D_{2i}$ in VIEW 1 and data input from its adjacent element $D_{1i}$ in VIEW 2. Generally the weighting factors for the two input elements will vary inversely with the relative distances of the respective centroids of the two elements from point 50. These weighting factors will generally be the same, however, for all points (at varying values of R) along the periphery of the slice at position $Z_0$. If the fan beam data is rebinned into parallel beam data an adjustment of the weighting for different positions on the fan may be desirable. However, such adjustments generally quite small.

In alternative embodiments of the present invention, greater numbers of input elements may be included in the weighted sum to determine the effective attenuation value at point 50, so as to improve the quality of the image, using Z-axis weighting or filtering methods known in the art. Furthermore, the attenuation data from array 30 may be reformatted, as is known in the art, from the fan beam format in which the attenuation signals are received, as exemplified in FIG. 1, to a parallel beam format, for the purpose of improving the quality of the resultant CT image. It will be understood that the methods described herein with reference to elements 23 and the unreformatted data received are preferably applied to such reformatted data samples.

Although point 50 at position $Z_0$ is shown in FIG. 2A as being midway between rows 27 and 29, it will be understood that the method described above may be applied to determine effective attenuation values at any Z-position in between rows 27 and 29 or within the detection area of one of the rows. In the particular case in which the Z-position of point 50 is substantially centered within one of the rows, the effective attenuation value at the point is preferably derived directly from the attenuation data in that row. Alternatively, the effective attenuation value may be calculated by taking a weighted average of the data in the row within which point 50 is centered with data from neighboring rows on either side thereof.

Figure 2B:
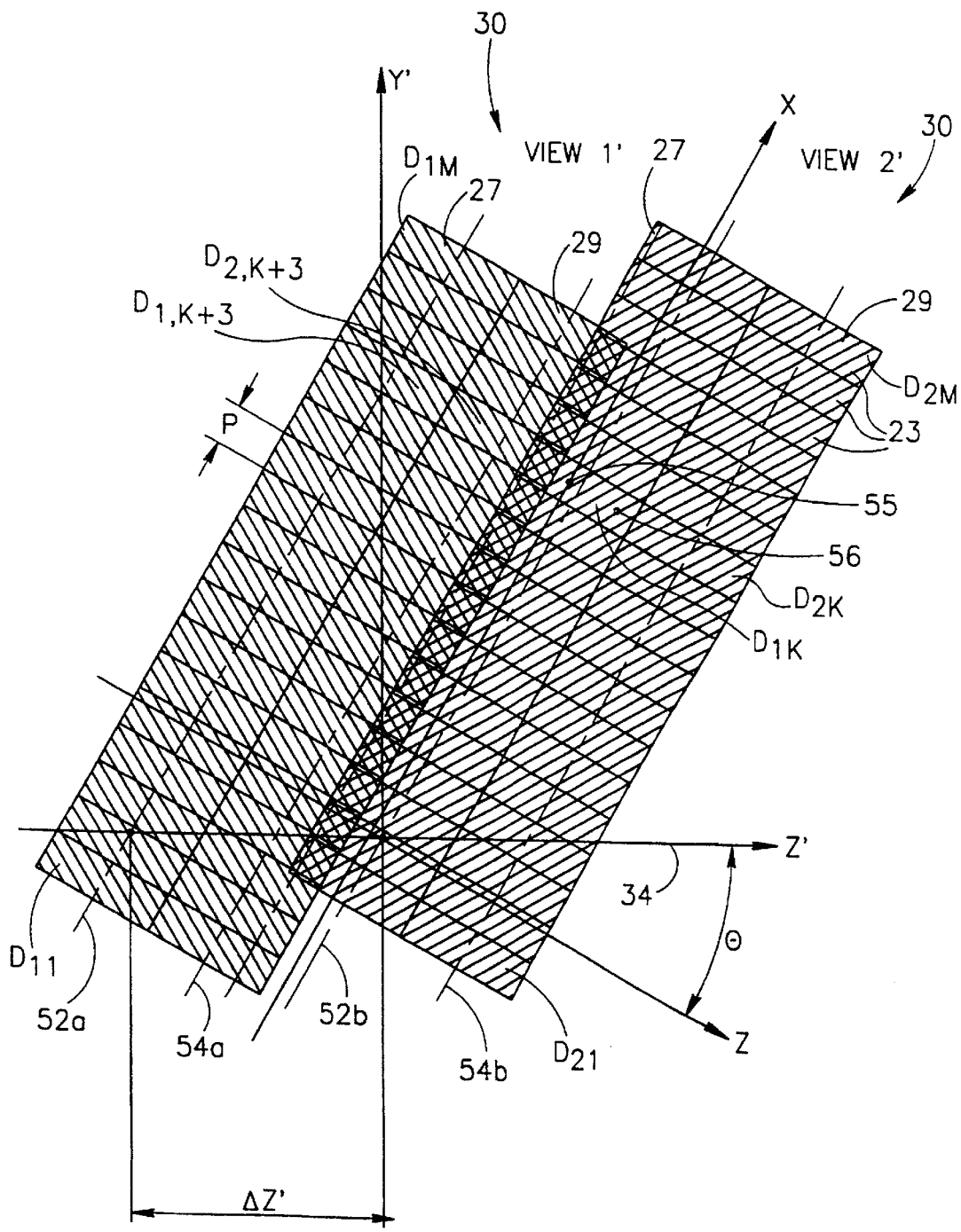
FIG. 2B is a schematic representation of the detector elements of FIG. 2A, at a second rotation angle (90 or 270 degrees) of the scanner, further illustrating geometrical principles applied in a preferred embodiment of the present invention.

FIG. 2B schematically represents the positions of detector elements 23 in the same configuration of scanner 20 as in FIG. 2A, i.e., with tilt angle θ. Two views, labeled VIEW 1' and VIEW 2', are acquired in the manner described above regarding VIEW 1 and VIEW 2, with tube 28 taken to be at rotational angles $\phi=90°$ and $\phi=450°$, respectively. Viewed from this substantially horizontal view angle, the Z-axis of gantry 32 is seen to be tilted with respect to the Z'-axis of bed 24, and the positions of elements 23 of array 30 in the two views are mutually offset along the X-axis. Moreover, since bed 24 has advanced along the Z'-axis direction relative to its position in VIEW 1 and VIEW 2, the X-axis, coinciding with the plane of the image to be reconstructed, is shown in FIG. 2B as having shifted in the Z'-direction.

For the purposes of the description that follows, we note further in FIG. 2B that elements 23 of array 30 are taken to have a common pitch P. Each of the two rows 27 and 29 of array 30 has a respective longitudinal axis passing substantially through the centroids of the elements in the row, which axes are marked 50θ2a and 54a respectively for VIEW 1', and 52b and 54b respectively for VIEW 2'. Bed 24 advances through gantry 32 at a velocity V, and the period during which the gantry makes a complete, 360° rotation is Δt, so that between VIEW 1' and VIEW 2', array 30 advances by a distance ΔZ' along the Z'-axis, as shown in FIG. 2B, given by ΔZ'=V·Δt. In the plane of the gantry, the distance is ΔZ =V·Δt cos θ.

Figure 3:
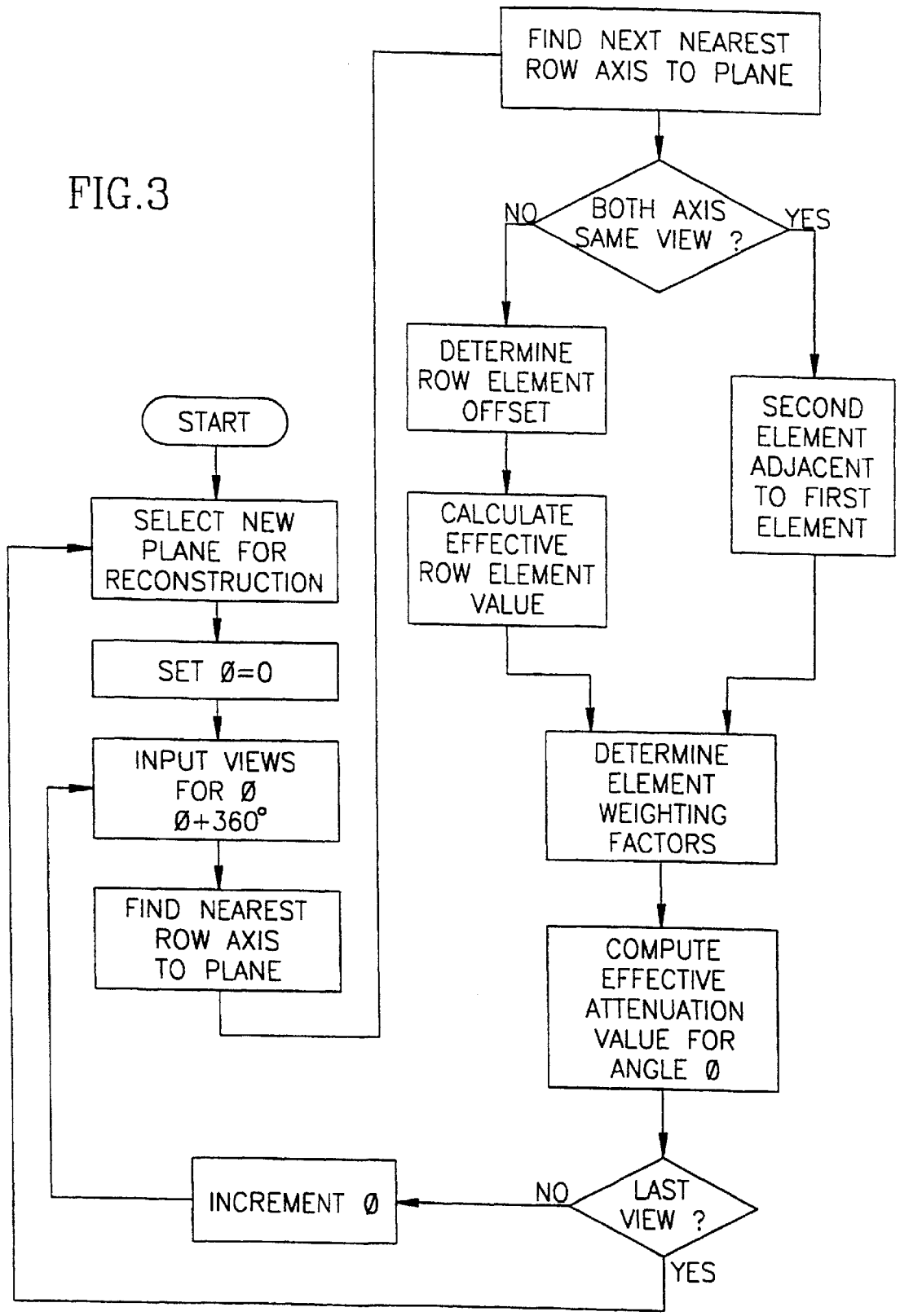
FIG. 3 is a flow chart illustrating a method for reconstruction of a CT image, in accordance with a preferred embodiment of the present invention.

FIG. 3 is a flow chart illustrating a method for calculating effective attenuation values in a planar image slice in the X-Y plane, generally perpendicular to the rotation axis of gantry 32, in accordance with a preferred embodiment of the present invention. The key steps in this method involve taking a plurality of effective detection points in the periphery of the plane, as described above, and then selecting and calculating appropriate input data from elements 23 to determine the effective attenuation values at each of the plurality of points.

The process of selecting and calculating the effective attenuation values is repeated at each of a plurality of gantry rotation angles φ. For each rotation angle, at least two attenuation signal matrices, from respective views at angles φ and φ+360° (or φ and φ+180° in the case of 180° reconstruction), are used in the calculation. In order to avoid the creation of image artifacts, for each angle it is generally necessary to select different input elements to correspond to each effective detection point and to determine appropriate weighting factors to use in interpolatively calculating the effective attenuation values at the points.

For example, when φ=90°, as shown in FIG. 2B, image reconstruction circuitry 40 receives the coordinates of rows 27 and 29 in VIEW 1' and VIEW 2' from system control unit 46 (shown in FIG. 1). The circuitry compares the Z-axis position of the plane for reconstruction, marked by the X-axis, with the positions of rows 27 and 29 to determine which of axes 52a, 54a, 52b and 54b is closest to the plane. In the case shown in FIG. 2B, axis 52b in VIEW 2' is the closest. If two axes are equidistant from the plane, then either may be chosen as the closest, and the remainder of the calculation is substantially unaffected.

Next the circuitry determines which of the remaining row axes is the next closest to the point. For some rotation angles φ, the next closest axis is from the same view as the closest axis. Such would be the case, for example, with regard to a plane passing through point 56 in FIG. 2B, for which axis 54b is the next closest. The corrected attenuation value at point 56 is then determined simply by weighted interpolation between elements $D_{1,k}$ and $D_{2,k}$, with the weighting factors dependent on the relative distances of axes 52b and 54b from point 56.

Returning now to consider point 55 on the X-axis, the next closest axis after axis 52b is axis 54a of row 29 in VIEW 1'. Element $D_{2,k+2}$ in VIEW 1' is closest to point 55 in its detection area, but the border between this element and its neighboring element in array 30, $D_{2,k+1}$, is offset relative to the borders between element $D_{1,k}$ and its neighboring elements in VIEW 2'. In order to avoid producing artifacts in the image that is reconstructed by circuitry 40, an effective row element attenuation value is calculated by weighted interpolation between the attenuation values of elements $D_{2,k+1}$ and $D_{2,k+2}$ in VIEW 1'. Weighting factors for this interpolation are calculated based on the relative offset of elements 23 of array 30 between VIEW 1' and VIEW 2'. This effective row element attenuation value is then combined by weighted interpolation with the value of the first input element (in this case $D_{1,k}$ in VIEW 2') to compute the effective attenuation value at point 55.

The following formula is a general expression for calculating the effective row element attenuation value $V_{eff}$ for the case where the first element $D_{1,k}$ is from VIEW 2' and $V_{eff}$ is to be determined by interpolation among the attenuation values $V_{2,i}$ and $V_{2,i+1}$ received respectively from two elements $D_{2,i}$ and $D_{2,i+1}$ in VIEW 1':

$$V_{eff}=V_{2,k} \text{ for } M-1-\Delta Z' \cdot \sin \Theta/P \leq k < M-1$$

$$V_{eff}=W_m V_{2,m}+W_{m+1}V_{2,m+1} \text{ for } 0 \leq k < M-1-\Delta Z' \cdot \sin \Theta/P$$

where m=INT[k+ΔZ'·sin Θ/P], and $W_m$ and $W_{m+1}$ are interpolation weighting factors, and INT(x) is the greatest integer in x. Although for the specific case illustrated in FIG. 2B, Θ=θ, where θ is the tilt angle of bed 24, the formulas above may be generalized to include both the swivel angle of bed 24 and the tilt angle of gantry 32 by substituting:

$$\Theta=\arcsin[\sin(\text{swivel}) \cdot \cos \phi + \sin(\text{tilt}) \cdot \sin \phi].$$

Preferably, the weighting factors $W_m$ and $W_{m+1}$ are calculated for linear interpolation, for example by the following formulas:

$$W_m=\Delta Z' \cdot \sin \Theta/P - INT(\Delta Z' \cdot \sin \Theta/P)$$

$W_{m+1}=1-W_m$

Alternatively, the weighting factors may be calculated using a shift function, for example:

$W_m=INT\{0.5+\Delta Z' \cdot \sin \Theta/P - INT(\Delta Z' \cdot \sin \Theta/P)\}$ $W_{m+1}=1-W_m$ Other weighting factors may similarly be used, such as, but not limited to utilizing more elements per row, depending, inter alia, on geometrical considerations in the CT scanner.

Similar formulas may be straightforwardly derived from the above equations for cases in which the first element (i.e., the element nearest to the point of interest in the planar corrected slice) is in VIEW 1', and an effective row element attenuation value must be determined by interpolation between elements in the preceding VIEW 2'.

In other preferred embodiments of the present invention, effective row attenuation values are calculated for the row whose axis is nearest the plane of the planar corrected slice, as well as for the row whose axis is next-nearest the plane. In this case, for example, an effective row attenuation value for row 27 could be calculated with respect to point 55 by weighted interpolation between elements $D_{1,k}$ and $D_{1,k-1}$ in VIEW 2'. The value would then be combined by weighted interpolation with the value of $V_{eff}$ determined for row 29 in VIEW 1', as described above, to calculate the effective attenuation value for point 55.

Additionally or alternatively, in some preferred embodiments of the present invention, data from more than two rows may be combined by interpolation to determine effective attenuation values for a planar corrected slice. For example, data from both of rows 27 and 29 in both VIEW 1' and VIEW 2' could be thus combined, and data from additional views at $\phi=+360 \cdot N°$ (or $+180-N°$ for 180 degree reconstruction) could also be introduced, in determining the effective attenuation value for point 55. In these preferred embodiments, the respective offset of each of the rows is taken into account, and interpolative weighting factors are calculated accordingly, based on the principles described above.

It will be appreciated that although the above preferred embodiments have been described, for simplicity, in terms of a two-slice scanner, based on detector array 30 having two rows of elements 27 and 29, the principles of the present invention are equally applicable to single-slice scanners, as well as to multi-slice scanners and arrays having three, four or more rows of elements.

Furthermore, the above preferred embodiments have been described with reference to 360° image reconstruction, in which the planar corrected slice is produced by interpolating between two views taken at adjacent positions of X-ray tube 28, between which the tube has made a full circle of rotation around bed 24. It will be appreciated, however, that the inventive principles described above may similarly be applied to 180° image reconstruction systems, as are known in the art. In such systems, the effective attenuation values are calculated from data acquired in two views that are 180° apart. Generally, an additional offset is introduced between array elements 23 in the two views, and the formulas given above for calculating $V_{eff}$ are preferably corrected to account for this offset.

It will also be appreciated that while the above preferred embodiments have been described with regard to medical CT imaging system 20, which is pictured as a third-generation system, forming an image of the body of human subject 22, the principles of the present invention may similarly be applied to fourth-generation and other types of CT imaging systems for medical and non-medical purposes.

It will additionally be appreciated that the preferred embodiments described above are cited by way of example, and the full scope of the invention is limited only by the claims.

What is claimed is:

1. A method for reconstructing images of an object in a variable-angle helical-scan CT scanner, said scanner including an X-ray tube mounted for rotation about a rotation axis, a detector array having one or more rows of detector elements that generate signals responsive to X-rays incident thereon, and a surface, translatable along a translation axis, on which surface the object is placed, said method comprising:

(a) angling the translation axis and the rotation axis at an acute angle relative to one another;

(b) rotating the X-ray tube about the rotation axis while translating the surface along the translation axis through a plane of rotation of the tube, whereby the X-ray tube describes a helical path relative to the object;

(c) acquiring first, second and optionally additional views at the same effective rotational angle about the axis of rotation, said views comprising X-ray attenuation data received from elements of the array;

(d) producing a planar corrected view at a given image slice position by interpolation of the data in at said first, second and optionally additional views, wherein the data is generated by non-corresponding elements in different views; and (e) repeating (a)–(d) at a plurality of rotational angles of the X-ray tube, for the given slice position; and (f) reconstructing an image of the slice from planar corrected views taken over a given range of view angles;

wherein images taken at angle separated by integral multiples of 180 or 360 degrees, depending on the range of view angles, are defined as being taken at the same effective angle.

2. A method according to claim 1, wherein producing the planar corrected view comprises:

finding a first row of detector elements in one of the first and second views having a longitudinal axis that is closest to a plane of the image slice;

finding a second row of detector elements in one of the first and second views having a longitudinal axis that is next closest to the plane after the first row;

determining a first attenuation value from the first row of elements and a second attenuation value from the second row of elements; and calculating an effective attenuation value by weighted interpolation of the first and second attenuation values.

3. A method according to claim 2, wherein finding first and second rows of detector elements comprises finding two adjoining rows of the detector array in one of the first and second views.

4. A method according to claim 2, wherein finding first and second rows of detector elements comprises finding a first row in the first view and a second row in the second view, and wherein determining first and second attenuation values comprises determining an offset between the first and second rows.

5. A method according to claim 4, wherein determining the offset between the first and second rows comprises determining an offset dependent on the rotational angle of the X-ray tube.

6. A method according to claim 4, wherein determining the offset between the first and second rows comprises determining an offset dependent on the acute angle between the translation axis and the rotation axis.

7. A method according to claim 4, wherein determining the first attenuation value comprises computing a weighted sum of attenuation data received from two or more detector elements in the first row.

8. A method according to claim 4, wherein determining the second attenuation value comprises computing a weighted sum of attenuation data received from two or more detector elements in the second row.

9. A method according to claim 2, wherein calculating the effective attenuation value by weighted interpolation comprises determining weighting factors dependent on the rotational angle of the X-ray tube.

10. A method according to claim 2, wherein calculating the effective attenuation value by weighted interpolation comprises determining weighting factors dependent on the acute angle between the translation axis and the rotation axis.

11. A method according to claim 2, wherein determining the first attenuation value at a point in the view comprises finding the two elements in the first row whose centroids are closest to the point and calculating an effective row element attenuation value based on signals received from the two elements.

12. A method according to claim 2, wherein determining the second attenuation value at a point in the view comprises finding the two elements in the second row whose centroids are closest to the point and calculating an effective row element attenuation value based on signals received from the two elements.

13. A method according to claim 2, and comprising finding one or more additional rows of detector elements, parallel to the first and second rows, and determining one or more additional attenuation values from the additional rows, wherein calculating an effective attenuation value in the planar slice comprises calculating the effective attenuation value by weighted interpolation of the additional values with the first and second attenuation values.

14. A method according to claim 1, and comprising acquiring one or more additional views at the same effective rotational angle as the first and second views, wherein producing the planar corrected image slice by interpolation of the data in the views comprises combining the one or more additional views with the first and second views by weighted interpolation of the data.

15. A method according to claim 1 wherein the detector array has one row of elements.

16. A method according to claim 1 wherein the detector array has more than one row of elements.

17. A method according to claim 1 wherein acquiring said first and second views comprises acquiring said first and second views at first and second positions along the helical path of the X-ray tube.

18. A method according to claim 1 wherein the object is a human subject.

19. A method according to claim 18 wherein the surface is a bed on which the subject lies.

20. A method for reconstructing images of an object in a variable-angle helical-scan CT scanner, said scanner including an X-ray tube mounted for rotation about a rotation axis, a detector array having one or more rows of detector elements that generate signals responsive to X-rays incident thereon, and a surface, translatable along a translation axis, on which surface the object is placed, the method comprising:

(a) angling the translation axis and the rotation axis at an acute angle relative to one another;

(b) rotating the X-ray tube about the rotation axis while translating the surface along the translation axis through a plane of rotation of the tube, whereby the X-ray tube describes a helical path relative to the object;

(c) acquiring first, second and optionally additional views of the object at the same effective rotational angle about the axis of rotation, said views comprising X-ray attenuation data received from elements of the array;

(d) producing a planar corrected view at a given image slice position by interpolation of the data in said first, second and optionally additional views; and (e) repeating (a)–(d) at a plurality of rotational angles of the X-ray tube for the given slice position; and (f) reconstructing an image of the slice from planar corrected views taken over a given range of view angles; and wherein images taken at angle separated by integral multiples of 180 or 360 degrees, depending on the range of view angles, are defined as being taken at the same effective angle, wherein determining a value for interpolation at a point in the view comprises finding the two elements in a row whose centroids are closest to the point and calculating an effective row element attenuation value based on signals received from the two elements.

21. A method according to claim 20 wherein acquiring said first and second views comprises acquiring said first and second views at first and second positions along the helical path of the X-ray tube.

22. A method according to claim 20 wherein the object is a human subject.

23. A method according to claim 22 wherein the surface is a bed on which the subject lies.

* * * * *